United States Patent [19]

Ward

[11] 4,090,954
[45] May 23, 1978

[54] METHOD FOR OXIDIZING MERCAPTANS AND MERCAPTIDE COMPOUNDS FROM AQUEOUS ALKALINE SOLUTIONS AND HYDROCARBON DISTILLATES

[75] Inventor: Clifford Ward, Louisa, Ky.

[73] Assignee: Ashland Oil, Inc., Ashland, Ky.

[21] Appl. No.: 753,400

[22] Filed: Dec. 22, 1976

[51] Int. Cl.$^2$ ............................................. C10G 27/06
[52] U.S. Cl. ..................................... 208/206; 252/428; 260/608; 423/183; 252/430; 252/431 N
[58] Field of Search ................ 208/206, 207; 252/428; 260/608

[56] References Cited

U.S. PATENT DOCUMENTS 3,252,892  5/1966  Gleim .................................. 208/206
3,923,645  12/1975  Anderson, Jr. et al. ............. 208/206

Primary Examiner—George Crasanakis
Attorney, Agent, or Firm—Van D. Harrison, Jr.

[57] ABSTRACT

Disclosed is a catalyst and method for converting mercaptans and mercaptide compounds in aqueous alkaline solution to disulfides. Catalytic agent is a metal complex synthesized from 3,3',4,4'-benzophenonetetracarboxylic dianhydride and converted to either the alkali metal salt or to the acid form. The method for oxidizing the mercaptide compounds comprises contacting mercaptans and mercaptide compounds in aqueous alkaline solution with air in the presence of the catalyst and subsequently separating alkaline solution from the resultant disulfide compounds.

17 Claims, 2 Drawing Figures

METHOD FOR OXIDIZING MERCAPTANS AND MERCAPTIDE COMPOUNDS FROM AQUEOUS ALKALINE SOLUTIONS AND HYDROCARBON DISTILLATES

NATURE OF INVENTION

This invention relates to a novel method and a catalyst for oxidizing to disulfides the mercaptans contained in hydrocarbon distillates and mercaptan compounds present in aqueous caustic solutions used to sweeten hydrocarbon distillates.

PRIOR ART

When hydrocarbon distillates such as gasoline, naptha, jet fuel, kerosene, diesel fuel, or fuel oil, contain mercaptans and hydrogen sulfide, they are commonly referred to as "sour" and usually are unsatisfactory for their intended uses. Mercaptans have a highly offensive odor even in minor concentrations. Their presence in gasoline impairs its susceptibility to octane-improvement through adding compounds such as tetraethyl lead. When mercaptans are combusted they yield undesirable atmospheric contaminants in the form of sulfur oxides.

In present day processes hydrogen sulfide is first removed from a sour distillate by contacting it with a selective solvent such as monoethanol amine. Subsequently, the mercaptans are removed by contacting the sour distillate with an aqueous solution (usually sodium hydroxide) thereby converting the mercaptans to water-soluble mercaptides such as sodium mercaptides. The alkaline solution, when separated from the sweetened distillate, retains the alkali mercaptide compounds and is regenerated for recycling to the sweetening process by converting the mercaptides present to disulfides. The conversion or oxidation of the mercaptides to disulfides is extremely slow. Consequently, a catalyst to increase the rate of conversion to disulfides is used. Ordinarily the disulfides formed are then removed from the alkaline solution by extraction with a suitable solvent such as naphtha. In a variation of the basic process, a mixture of distillate, aqueous alkaline solution, and catalyst is contacted with air thereby converting mercaptans present to the disulfides. Sweetened distillate is recovered from the reaction products. These basic processes are sometimes combined in a two-step mercaptan-removal process.

U.S. Pat. No. 2,966,453 discloses a process for oxidizing mercaptans to disulfides with an oxidizing agent (air) in the presence of a metal porphyrin catalyst or metal azoporphyrin catalyst. Metal porphyrins have a structure as follows where M is a metal and R is a substituent group which may be hydrogen, or an alkyl, aryl or other substituent containing up to 30 or more substituent atoms.

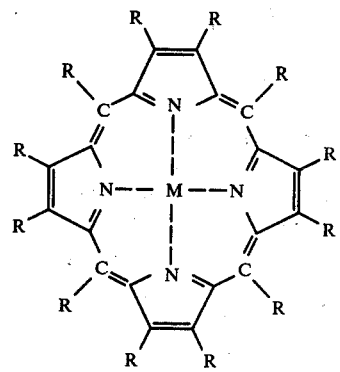

In the 2,966,453 Patent M preferably is cobalt or vanadium, but may be selected from a number of other metals.

Metal azoporphyrins have the following structure where M is a metal.

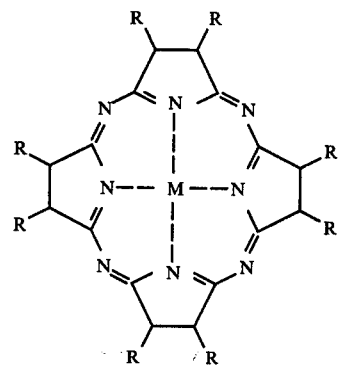

In the 2,966,453 Patent, M apparently again preferably is cobalt or vanadium, but may be selected from a number of other metals and R has the relationship stated previously. In the 2,966,453 Patent, because the metal porphyrins and azoporphyrins are not readily soluble in neutral or alkaline aqueous solutions, their sulfonated or carboxylated derivative is preferred.

U.S. Pat. Nos. 2,882,224; 2,988,500; 3,108,081; 3,230,180 and 3,148,156 relate to the use of phthalocyanine compounds as a catalyst in the oxidation of mercaptans or mercaptides in alkaline solution. The phthalocyanine compounds have a structural formula as follows where M preferably is cobalt or vanadium.

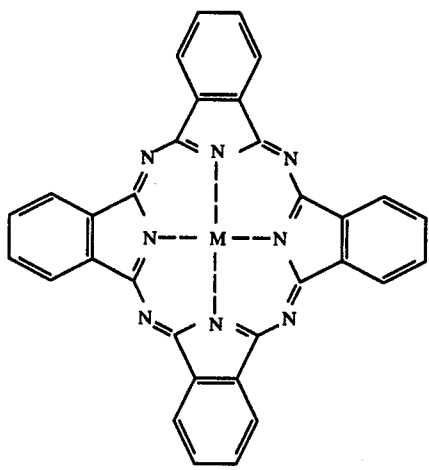

III

Again, the metal phthalocyanine is not readily soluble in aqueous solutions, so the sulfonated or carboxylated derivatives are indicated as preferred in the disclosures of these patents.

U.S. Pat. No. 3,923,645 discloses tetrapyridinoporphyrazine-metal-complex catalysts having the structural formula:

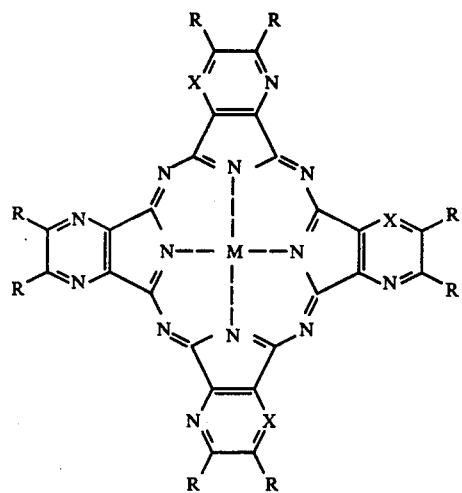

IV where M is selected from a number of metals including copper and vanadium. The R group may be hydrogen, or an alkyl or aryl group, or two adjacent R groups may be constituents of a cyclic or aromatic carbon structure. In the same compound the R groups may be all identical or all different. N is nitrogen. X is a nitrogen atom or is a carbon atom having one R group attached thereto. When all the Rs are hydrogen and X is a carbon atom, the unsubstituted metal tetrapyridinoporphyrazine compound is defined. This compound is deposited on an inert granular carrier. Spent caustic containing alkali mercaptide compounds is contacted with oxygen (air) in the presence of the impregnated inert granular carrier thereby oxidizing the mercaptides to the disulfide form. Although this catalyst works well, regeneration of the spent catalyst has sometimes proved difficult. Metal oxides, particularly iron oxide, and the disulfides formed from oxidation of the mercaptide compounds gradually coat the granular catalyst carrier occluding oxygen and making regeneration more difficult.

SUMMARY OF THE INVENTION

Briefly stated, this invention comprises in one aspect: (a) a method for oxidizing mercaptides to disulfides by contacting said mercaptides with an oxidizing agent (preferably air) in an aqueous alkaline solution (preferably sodium hydroxide) of a catalyst comprising the acid form or the alkali metal salt form of a metal complex, 2,3,7,8,12,13,17,18-tetra [1,2-benzo-4 (4'phthaloyl)]-porphyrazine-2-22,23,24-tetraene or a substituted derivative thereof, (b) in a second aspect, a method for making the metal-complex catalyst, in another aspect; (c) the metal-complex catalyst product and (d) the catalyst product resulting by depositing the metal complex on an inert carrier such as granular activated carbon.

DETAILED DESCRIPTION OF THE INVENTION

Figure 1:
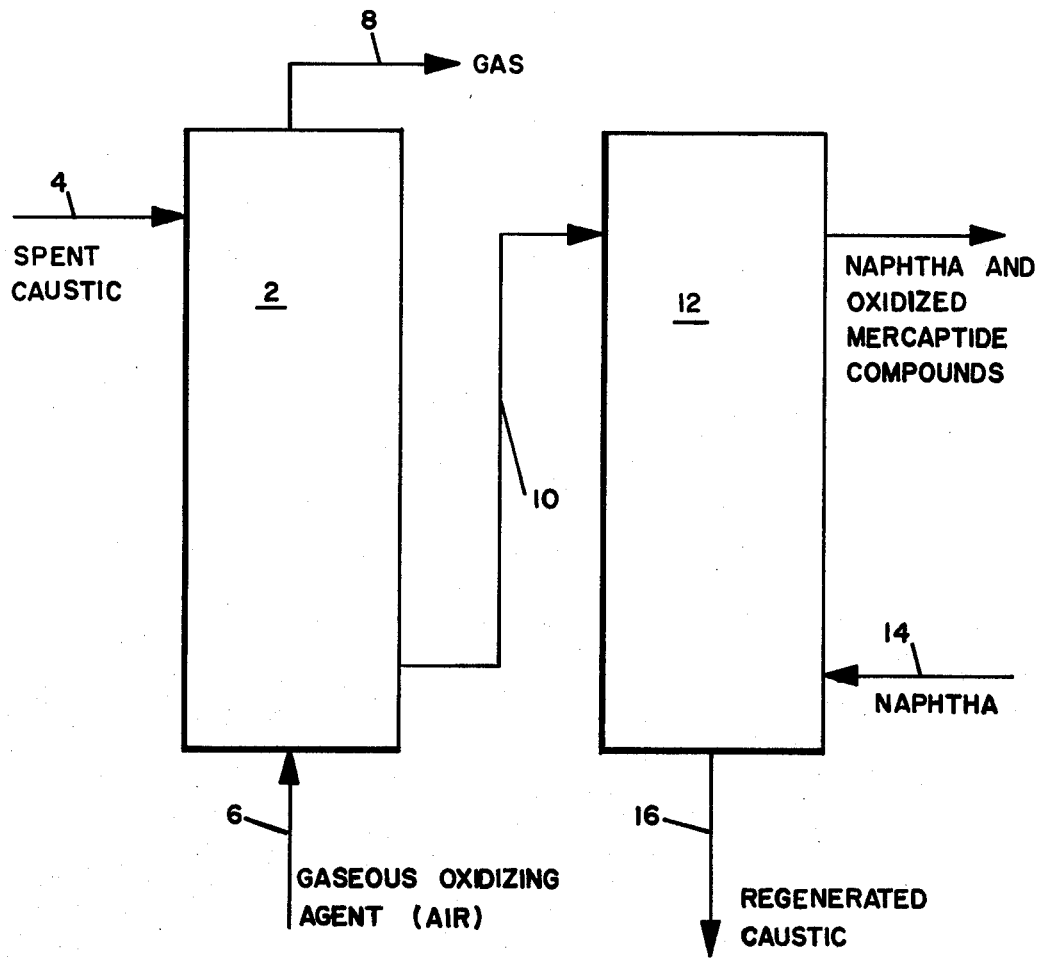
FIG. 1 is a flow sheet depicting one method of our invention wherein an alkaline solution containing alkali mercaptides and dissolved metal-complex catalyst of this invention is contacted with a gaseous oxidizing agent.

The following disclosure is arranged to show: (a) procedure for making the metal complex of this invention; (b) the method of oxidizing the mercaptans and mercaptides in an alkaline solution to disulfides by contacting them with oxygen in the presence of the metal complex of this invention and substituted derivatives thereof, the metal complex being dissolved in the solution, (c) the method of depositing the metal complex of the invention on an inert granular carrier and the catalyst resulting thereby, and (d) the method of oxidizing the mercaptans and mercaptides in an alkaline solution to disulfides by contacting them with oxygen in the presence of the granular carrier containing the deposited metal complex.

The metal complexes constituting the basis of our invention are the compounds in either the acid or the alkali metal salt form of the metal complex synthesized from 3,3',4,4'-benzophenonetetracarboxylic dianhydride and substituted derivatives thereof and are believed to have a structural formula as follows:

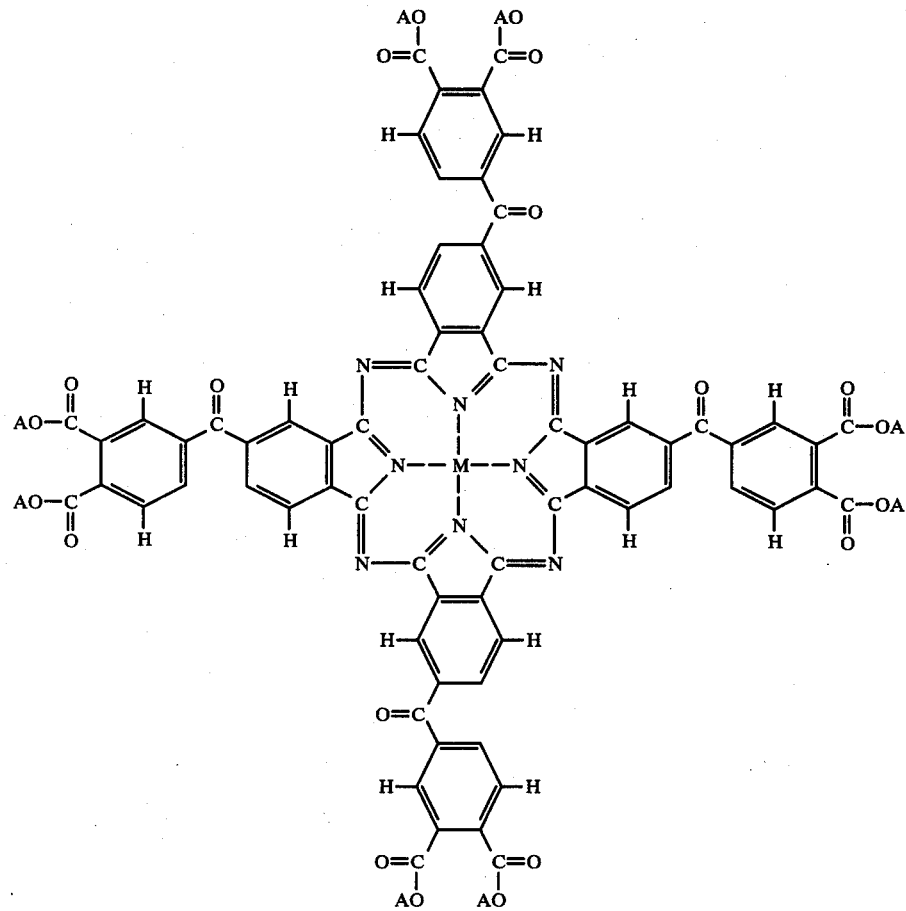

V where M is a metal selected from the group consisting of iron, manganese, chromium, magnesium, copper, nickel, zinc, titanium, hafnium, thorium, tin, lead, columbium, tantalum, antimony, bismuth, molybdenum, palladium, platinum, silver, mercury, vanadium and cobalt and A is hydrogen or an alkali metal. M preferably is cobalt or vanadium and A, if an alkali metal, preferably is sodium or potassium. For purposes of brevity, if A is hydrogen the compound described hereinafter is referred to as the acid Me-BTDA complex. If A is an alkali metal the compound is designated as the alkali metal Me-BTDA complex. Similarly, the acid form of the cobalt and vanadium complexes will be designated as the acid Co-BTDA and Va-BTDA, respectively. Alkali metal salts of the cobalt and vanadium complexes will be described as alkali metal Co-BTDA and alkali metal Va-BTDA, respectively.

Of these compounds, the preferred compounds are the acid cobalt and acid vanadium-BTDA complexes because of their slightly greater solubility in aqueous caustic and because they are somewhat more easily processed. Of these two, the cobalt complex is the most preferred. The alkali metal salts, although less preferred, are still nevertheless useful, particularly the sodium and potassium salts of the cobalt-BTDA complex.

The acid cobalt-BTDA complex is believed to have the formula:

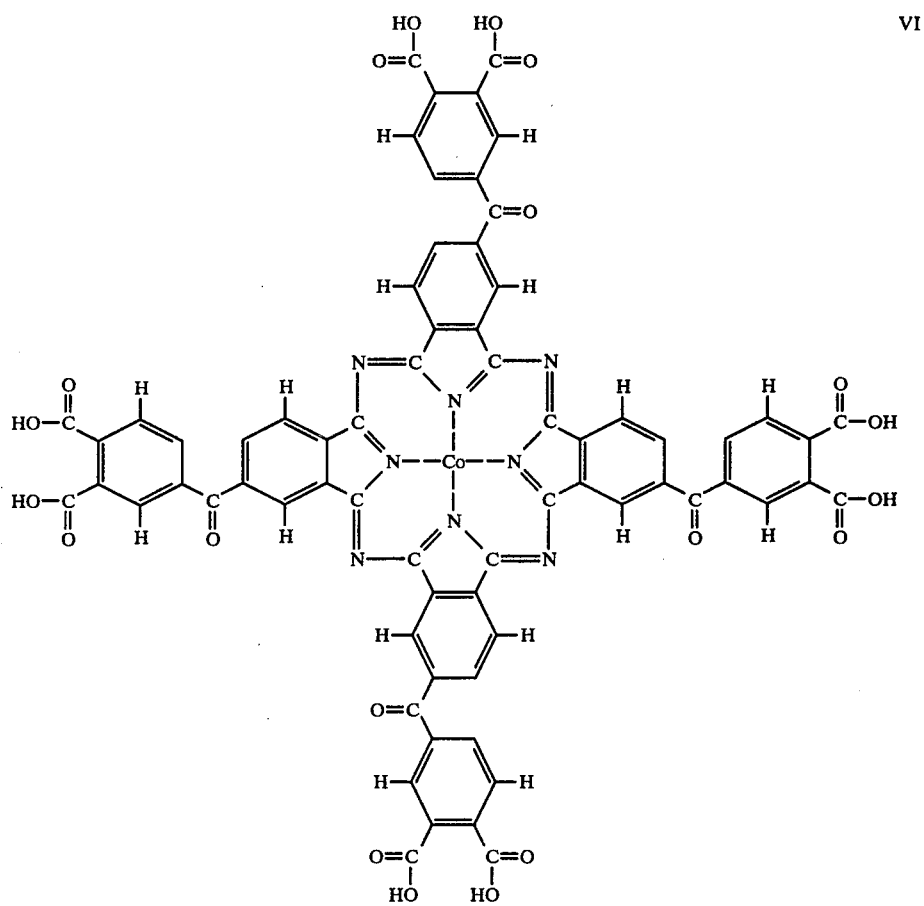
VI
The sodium salt of the cobalt-BTDA complex would have the formula:

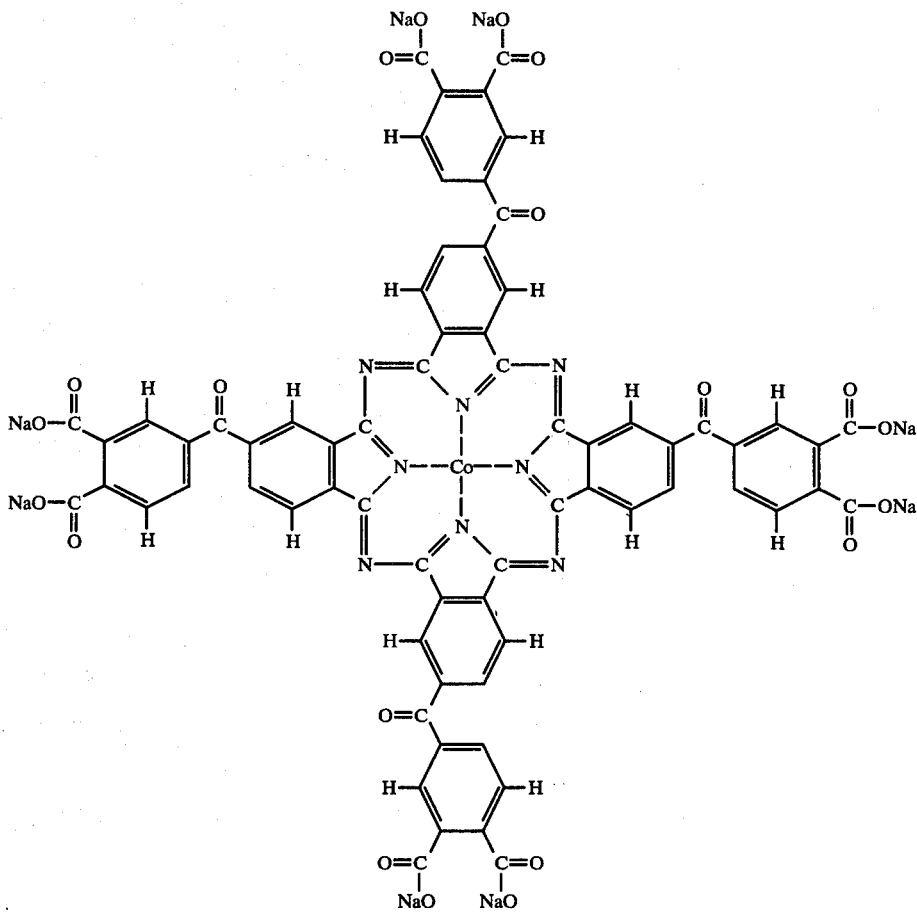

VII

PREPARATION OF METAL-BTDA COMPOUNDS

The reactants utilized initially in preparing the metal-BTDA complex are urea, a metal salt of the metal it is desired to complex, boric acid, ammonium molybdate and 3,3',4,4'-benzophenonetetracarboxylic dianhydride (also known as 4,4'-carbonyldiphthalic anhydride) having the structural formula:

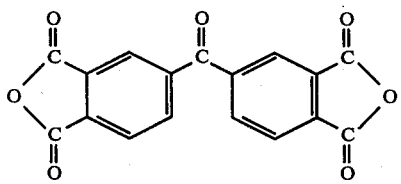  VIII

The reaction is conducted in the presence of a suitable solvent such as trichlorobenzene. The reactants are reacted in preferred stoichiometric mole proportions as follows:

|  | Max. | Min. | Preferred |
|---|---|---|---|
| 3,3',4,4'-benzophenone-tetracarboxylic dianhydride | 1.0 | 1.0 | 1.0 |
| Urea | 20.0 | 1.0 | 16.0 |
| Metal Salt | 1.0 | 0.1 | .04 |
| Boric acid | 1.0 | 0.1 | .33 |
| Ammonium molybdate | 1.0 | 0.002 | .01 |

The reactants preferably are mixed in the liquid carrier and the temperature maintained between 190°–220° C. The reaction is endothermic so that it will be necessary to supply heat. Preferably the reaction is conducted at pressures of 50 to 100 psig. The reaction can however be conducted at atmospheric pressure avoiding the necessity of using pressurized vessels. After sufficient time has elapsed to permit reaction, the reaction product is removed and purified. Purification is accomplished by pulverizing any lumps present, drying the resulting product to remove solvent, washing the powdered dried product with water to remove unreacted urea and other water soluble impurities, and drying the remaining undissolved powdered product. This purified product can be converted to a form soluble in aqueous alkaline solutions by either of two treatments. The purified product can be slurried with a strong base, preferably caustic, (sodium hydroxide), the mixture heated to evaporate excess water, and the dried product ground to a powder. The amount of base reacted should be that quantity necessary to insure conversion of the acid metal complex to the alkali metal salt form. This last material is then ready for use as the oxidation catalyst by adding it to the refinery caustic sweetening stream.

The most preferred method, however, of rendering the metal complex soluble in refinery alkaline sweetening streams is to convert it to the acid form by reacting it with a dilute aqueous mineral acid, preferably sulfuric acid in a concentration of 15–25 percent acid. Preferably the acid metal complex is refluxed with the acid for a period of time necessary to complete the conversion. During this period, ammonium sulfates are formed and any residual trichlorobenzene is removed by azeotropic distillation. The amount of acid used should be that amount necessary to convert the metal BTDA compound to the acid form. Following the refluxing step, the solid material remaining is washed with water and is then ready for use in a refinery caustic sweetening process.

EXAMPLE 1

Three separate batches of catalyst were prepared in three separate runs. In each run, 170 pounds (77.2 kilograms) of trichlorobenzene was first added to a reactor. To this was then added 16.7 pounds (7.6 kg.) of 3,3',4,4'-benzophenonetetracarboxylic dianhydride, 50 pounds (22.7 kg.) of urea, 6 pounds (2.7 kg.) of cobaltous chloride ($CoCl_2 \cdot 6H_2O$), 1 pound (0.45 kg.) of boric acid and 0.5 pounds (0.23 kg.) of ammonium molybdate. After these reactants had been thoroughly mixed, the temperature was raised to a temperature of 425° F. (218° C) over a period of about 3½ hours. The temperature was then maintained at about 425° F. (218° C.) for approximately 80 additional minutes. The reaction mass was then allowed to cool to ambient temperature over night with some continual stirring. The reaction product was then removed and purified.

In the purification step, any lumps in the reaction product were crushed and any solvent present in the product was removed by drying. The dried material was then ground to a fine powder and washed with water at room temperature to remove unreacted urea and other water soluble impurities. This water-washed product was next dried at a temperature of 266° F. (130° C.). The dried material was then combined with aqueous sodium hydroxide, 45° Baume, in a slurry and heated to a temperatue of 266° F. (130° C.) to effect conversion to the sodium salt and to remove the water. The resulting solid material was then cooled and ground. The average yield of the finished product, (sodium salt of Co-BTDA), per run was 44.3 pounds. This material contained a ratio by weight of NaOH to Co-BTDA of 1.5 to 1 and was approximately 73.4 percent NaOH and 26.6 percent the sodium salt of Co-BTDA complex.

EXAMPLE 2

In this example, all reactions were conducted at atmospheric pressure. Into a two-liter reactor equipped with a mechanical stirrer, condenser, thermowell, and thermocouple was charged 900 ml. of trichlorobenzene. To this was added 0.259 gram moles of 3,3',4,4'-benzophenonetetracarboxylic dianhydride, 2.367 gram moles of urea, 0.095 gram moles of cobaltous chloride, 0.081 gram moles of boric acid and 0.002 gram moles of ammonium molybdate. The reaction mixture was slowly heated to a temperature of between 100° C. and 135° C. at which temperature the urea decomposed evolving ammonia and other gases. Heating was slowly continued until a reflux temperature of about 211° C. was reached. The reaction mixture was allowed to reflux at this temperature for 2 hours. Heating was then discontinued and the temperature of the mixture was allowed to decrease to about 125° C. At this point the reaction mixture was vacuum distilled at a pressure of 50 mm. of mercury until the reactor and its contents were dry. The residue was 135 grams of a dry granular material. This material was then slurried with 1000 ml. of water containing 3 percent of dissolved ammonia for 30 minutes at a temperature of 90° C. The slurry was filtered and the solid residue washed with acetone (100 ml.) and dried at 150° C., yielding 105 grams of product.

This dried product was then converted to the sodium salt by mixing it with 355.5 grams of 42° Baume caustic (39% NaOH and 61% $H_2O$) and heating in an oven at 150° C. for about 20 hours. The yield was about 126 grams of the sodium salt.

Although I do not wish to be bound by any theory, I believe the product obtained was the sodium salt of the cobalt complex having the structrual formula:

IX

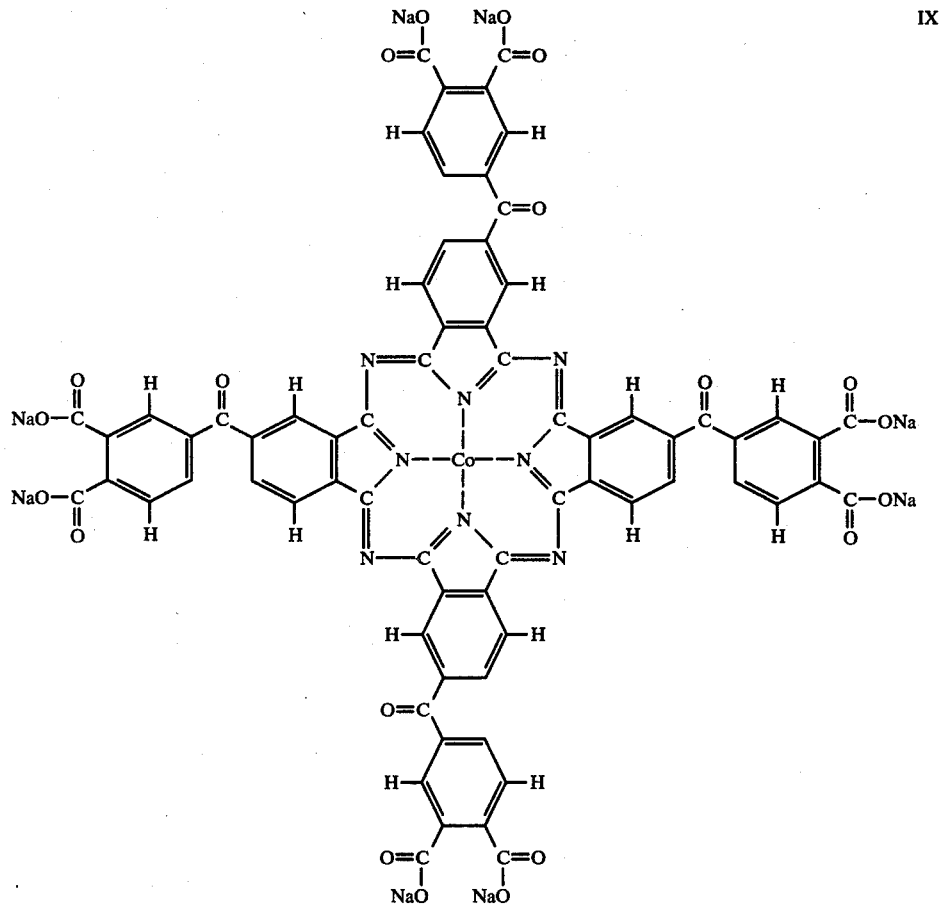

EXAMPLE 3

Approximately 101 grams of Cobalt-BTDA complex were prepared in the manner described in Example 2. This product was then slowly added with stirring to 510 milliliters of a 15 to 25 percent by weight aqueous solution of sulfuric acid. The mixture was refluxed at a temperature of 104° C. for approximately 4 hours, cooled to 90° C. and filtered to recover the solid material present. This material (the desired acid Cobalt-BTDA complex) was washed with water (2,500-ml. portions) and dried at 100° C. The resulting dried product was graular, free flowing, non-hygroscopic and readily soluble in dilute caustic solutions. The amount of solid Cobalt-BTDA acid catalyst obtained was 72.6 grams.

Again, although I do not wish to be bound by any theory, I believe the product obtained was acid Cobalt-BTDA complex having the structural formula:

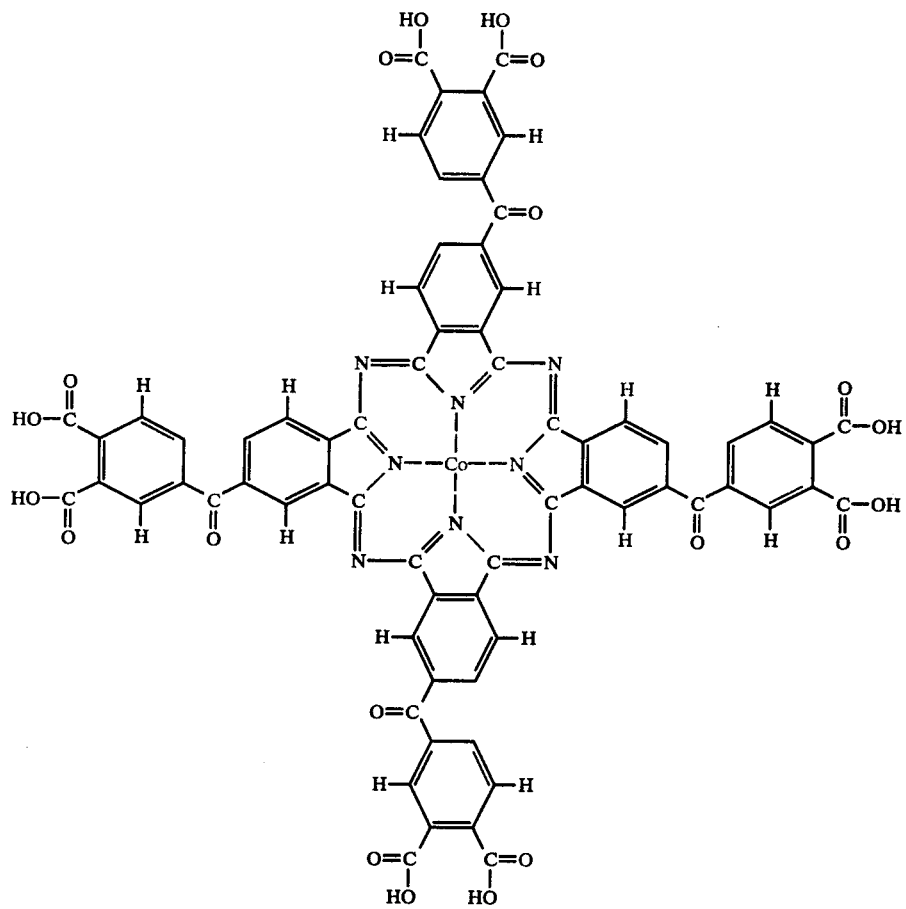

EXAMPLE 4

Using a procedure similar to that of Example 1, the sodium salt of the vanadium-BTDA complex was prepared. Fifty grams of 3,3',4,4'-benzophenonetetracarboxylic dianhydride, 150 grams of urea, 15 grams of vanadium pentoxide, 2 grams of boric acid and 1 gram of ammonium molybdate were combined in 400 milliliters of trichlorobenzene. The reaction mixture was heated to a temperature of about 218° C., over a period of 90 minutes. It was maintaned at this temperature for approximately 1 hour and was then cooled to 100° C., over a period of another hour.

The reaction product was then blended with 5 liters of hot water and filtered. The granular residue retained on the filter medium was then dried at 105° C. providing a final weight of product of 66.2 grams. A portion of this vanadium-BTDA complex in the acid form was then hydrolyzed to the sodium salt by combining 30.0 grams of the dried complex and 100 ml. of 43° Baume caustic (39.2 weight per NaOH) and heating the mixture for approximately 20 hours at 150° C. Eighty grams of product were obtained. The product is believed to have been a mixture of excess caustic and the sodium salt of the vanadium-BTDA complex having the structure:

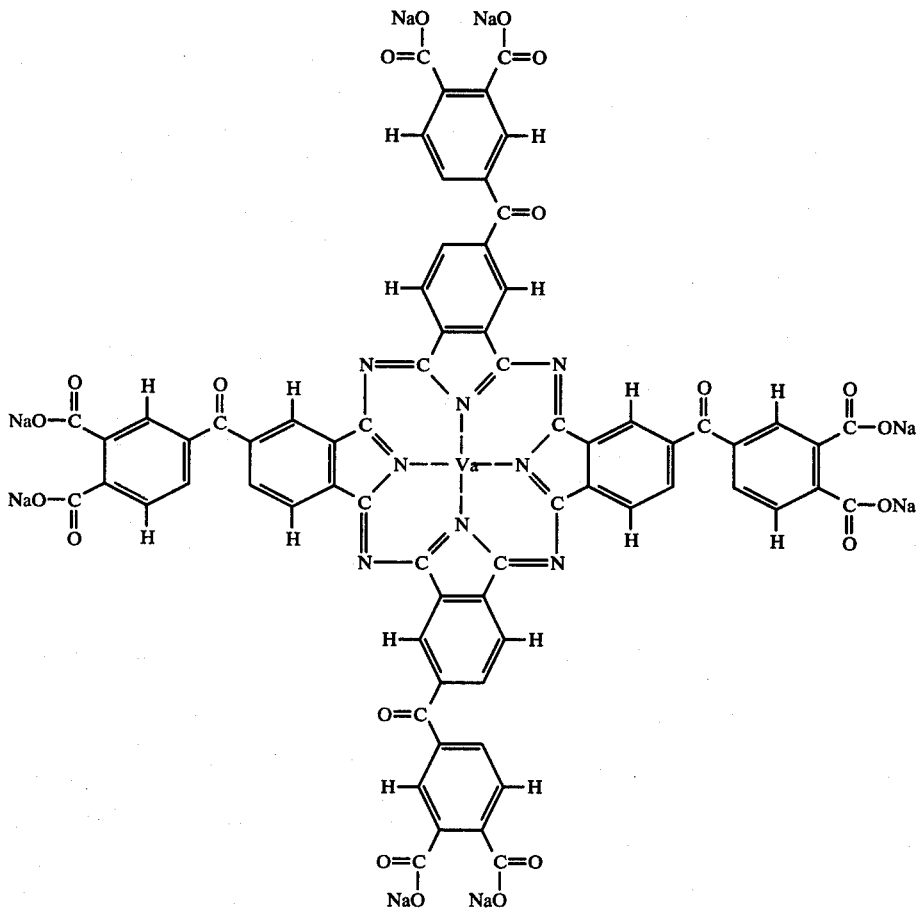

Use on Inert Carrier

Although it is preferred to use the acid complex or the alkali metal salt of the metal compound or complex having the general structural formula V in solution in the alkaline solution contaning alkali mercaptide compounds, the complex or compound can also be used in a form where it is deposited or supported on an inert granular carrier such as activated carbon.

The method for preparing the supported catalyst comprises: (1) forming an aqueous, alkaline solution of the alkali metal Me-BTDA complex; (2) adding the resultant solution to a suitable inert carrier, preferably in granular form; (3) allowing the carrier to soak in the solution at ambient temperature; (4) draining the unadsorbed solution from the carrier; and (5) washing the carrier with a neutral solvent, preferably water.

Any inert porous material may be used as a carrier providing it is inert to alkaline solutions, has sufficient porosity and surface area to retain the metal-BTDA complex or derivative thereof in effective amounts, and has sufficient resistance to crushing when placed in a packed column. Granular activated carbon is preferred. As for the solvent used initially to dissolve the complex, water can preferably be used or, a dilute aqueous solution of ammonia. It should be noted that the supported catalyst after the final washing need not necessarily be dried but may be put to use in a wet condition.

The amount of alkali metal Me-BTDA complex or derivative thereof deposited on the porous carrier will vary according to its concentration in the alkaline solution. It is preferred to deposit as much of the metal compound as possible on the carrier.

A supported catalyst containing between 0.5 and 2 percent by weight of metal compound or metal complex is effective, although even lower concentrations will have beneficial effect in oxidizing mercaptides to disulfides in an aqueous alkaline solution.

The following example is presented to demonstrate the method of preparing the supported catalyst.

EXAMPLE 5

Fifteen grams of a product prepared as in Example 1 and considered to contain 6 grams of the sodium salt of the Co-BTDA complex was dissolved in 1500 ml. of water and 15 ml. of an aqueous solution of ammonia. To the solution was added 600 grams of activated carbon of 8-30 mesh size (U.S. Sieve Series). The resultant mixture was allowed to sit overnight at room temperature and then decanted. The residue was washed with tap water and reserved for subsequent testing in a packed column, a procedure described in Example 8.

Oxidation of Mercaptans

Another embodiment of this invention comprises the process for regenerating in aqueous alkaline solution containing alkali mercaptide compounds by contacting the alkaline solution with an oxidizing gas, such as a mixture of oxygen and inert gas, or preferably air, in the presence of a catalyst comprising the acid form or the alkali metal salt of the metal compound or complex or substituted derivatives thereof of the previously described reaction product of 3,3',4',4-benzophenonetetracarboxylic dianhydride, urea and metal salt, having the general structural formula V shown above. The mercaptide compounds present in the aqueous alkaline solution are oxidized to disulfides. The disulfides are then removed from the aqueous alkaline solution by means well known to refining technology such as by extraction with naphtha. The regenerated caustic is then recycled to the hydrocarbon-treating process where it absorbs and reacts with more mercaptans to form alkali mercaptides. After this step, the spent caustic is recycled to the regeneration step just described.

The acid form or the alkali metal salt of the metal compound or complex is that corresponding to structural formula V. It is recognized, of course, that when the acid form is added to an aqueous refinery caustic stream, it is neutralized and converted to the alkali salt form in solution. In the acid form the cobalt and vanadium complexes are preferred and of these, the cobalt is the most preferred. In the alkali salt form, the sodium and potassium salts of the cobalt and vanadium-BTDA complexes shown in structural formulas IX and XI are preferred and of thse, the most preferred is the sodium salt of the cobalt-BTDA complex for regenerating spent caustic solutions containing alkali mercaptide compounds. The aqueous alkaline solutions used in the hydrocarbon sweetening process preferably are solutions of sodium hydroxide (hereinafter referred to as caustic) and of potassium hydroxide. Other alkaline solutions which can be used include those of lithium hydroxide, rubidium hydroxide and cesium hydroxide. However, for economic reasons, these last mentioned compound generally are not preferred.

Referring now to FIG. 1, reference numeral 2 designates a regeneration tank. At a point near the top of tank 2, spent aqueous caustic (sodium hydroxide) from a distillate-sweetening process (for example, a gasoline sweetening process) is introduced through line 4. The caustic ordinarily has a concentration of sodium hydroxide of between about 5 and about 25 percent by weight and contains between about 5 and about 5000 ppm of alkali mercaptides depending upon the concentration of mercaptans in the distillate being treated and the contact time between the caustic and sour distillate. For purposes of this invention, a concentration of catalyst equivalent to between 2 and 100 ppm, based on total weight of caustic sodium and catalyst added, and preferably between 10 and 15 ppm, of the complexing metal such as cobalt is maintained in solution in the aqueous caustic.

To illustrate, if the acid form of the Cobalt-BTDA complex is used, the weight percent of cobalt in the acid complex is 4.41 percent. (The molecular weight of the acid form of Cobalt-BTDA is calculated to be 1339). The weight of dried catalyst added (assuming no water of hydration present) to provide a cobalt concentration of 2 to 100 parts per million parts of catalyst and aqueous caustic would be between about 45 and 2300 parts per million parts total weight of catalyst and aqueous caustic solution. If the sodium salt of the Cobalt-BTDA complex is used, the weight percent of cobalt in the compound is 3.89%. (The molecular weight of the sodium salt of Cobalt BTDA is calculated to be 1515). The concentration of the sodium salt of Cobalt-BTDA corresponding to between 2 and 100 ppm of cobalt is approximately 50 to 2500 ppm of sodium salt of Cobalt-BTDA.

A gaseous oxidizing agent, preferably air, (although pure oxygen or oxygen diluted with non-reactive gases can be used) is introduced through line 6 and rises through tank 2 so that the spent caustic and gaseous oxidizing agents are mingled. Other means of mixing the spent caustic and gaseous oxidizing agent may be used prior to or at the time of admitting these materials to the regeneration tank 2. As the gaseous oxidizing agent, caustic solution and mercaptans and mercaptide compounds mingle in the regeneration tank, the mercaptide compounds react in the presence of the BTDA catalyst and oxygen to form the disulfides. At the top of the bed, gas is removed through line 8 and vented from the system. The spent alkaline solution now containing oxidized mercaptide compounds (organic disulfide) and a minimum of unoxidized mercaptans is carried through line 10 to scrubber 12 where naphtha introduced through line 14 and flowing up through scrubber 12 extracts the organic disulfides present in the caustic solution. The method of scrubbing alkaline solutions with naphtha to remove oxidized mercaptans is well known to those in the art and needs no further description here. Regenerated alkaline solution is recovered through line 16 and is returned to the distillate treating process.

The ratio of moles of oxygen admitted to the system to the moles of mercaptan admitted preferably is at least 0.25 to 1, but can be as high as 1 to 1. Operating pressures and temperatures in the regeneration zone 2 are between about 10 and about 100 psig (1.68 and 7.8 atmosphere) and about 50 and about 105 F. (10° to 66° C.) respectively.

Figure 2:
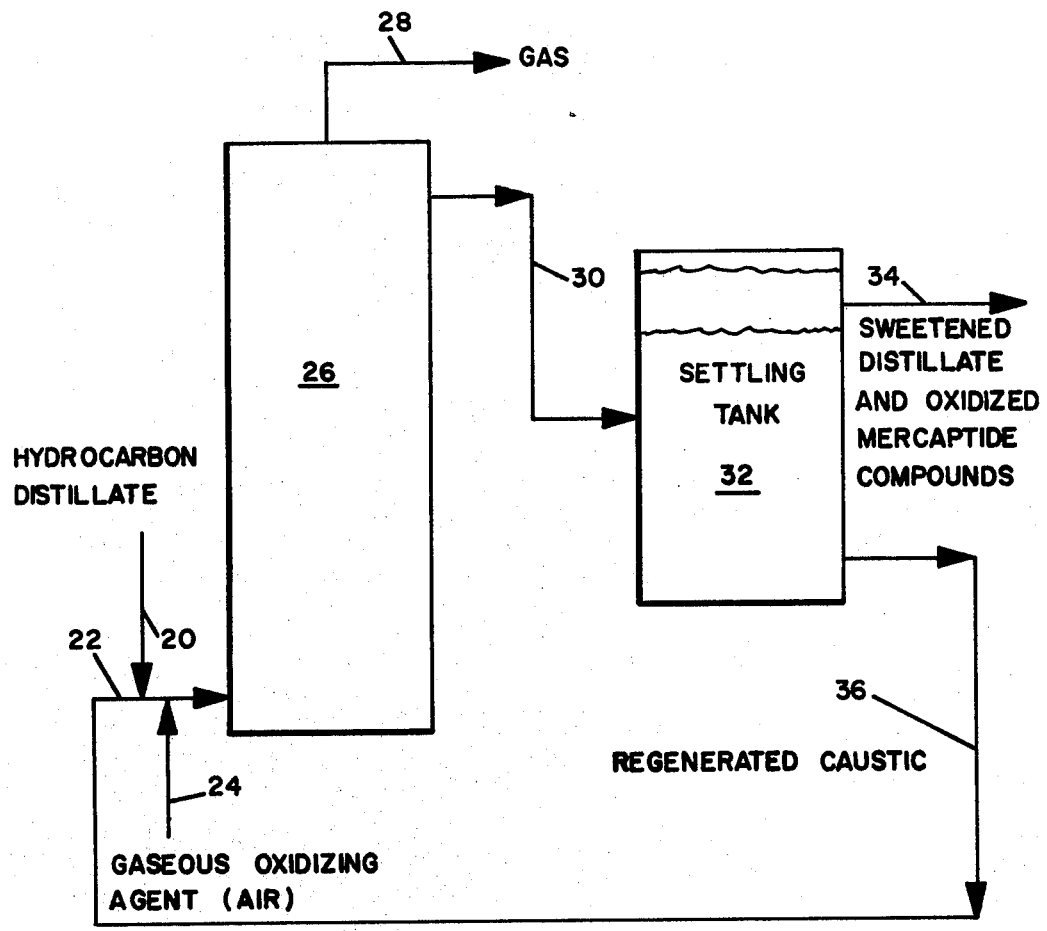
FIG. 2 is a flow sheet depicting another method of this invention wherein the hydrocarbon distillate containing mercaptans, a gaseous oxidizing agent, and alkaline solution containing the dissolved metal-complex catalyst are simultaneously contacted with each other.

FIG. 2 presents schematically a second embodiment of our invention which can be used when the mercaptans present in the hydrocarbon distillate are objectionable primarily because of their odor, and when the mercaptans, if converted to the less offensive disulfide, can remain in the final distillate product. In this embodiment, sour hydrocarbon distillate is introduced through line 20 into line 22 wherein regenerated alkaline solution (sodium hydroxide) containing the dissolved catalyst of this invention is flowing. A gaseous oxidizing agent, preferably air, is introduced through line 24 so that a mixture of air, sour distillate, and aqueous alkaline solution are carried through line 22 into the bottom or regeneration tank 26. The mixture of distillate, alkaline solution and air flows up through tank 26 to the top where gases present are removed through line 28. The mercaptan compounds present in the distillate are converted to organic disulfides which are soluble in the hydrocarbon distillate and are retained therein. The mixture of aqueous alkaline solution and hydrocarbon distillate flows through line 30 into settling tank 32. In settling tank 32 the hydrocarbon distillate now sweetened but still containing the oxidized mercaptan compounds is withdrawn through line 34. The alkaline solution which separates as a separate phase is removed through line 35 and is recycled to the sweetening process. The conditions of temperature, pressure and concentration of dissolved catalyst in the caustic for this embodiment of our invention are the same as for our first embodiment described.

Still another, less preferred, method of contacting spent caustic with a gaseous oxidizing agent and the metal complex salt of this invention is by flowing the aqueous spent caustic through a packed bed of the complex salt deposited on an inert granular carrier, similarly as described in U.S. Pat. No. 3,923,645 and 3,980,582 and under the conditions described therein. In this method, additional metal complex salt can then be added to the alkaline stream as its concentration therein diminishes. This will serve to maintain a maximum concentration of metal complex salt on the activated carbon.

Another method of contacting spent caustic with a gaseous oxidizing agent and the acid form as the alkali metal salt of this invention is by a batch process. In this variation, the caustic containing mercaptides and dissolved catalyst is agitated while the gaseous oxidizing agent is bubbled through the mixture. The mixture is then stripped of the oxidized mercaptides by conventional methods such as liquid-liquid extraction with naphtha. The regenerated caustic is then ready for recycling to the sweetening process. This method is, however, less desirable because of the difficulties associated with batch process in comparison to continuous processes.

The following examples are presented to demonstrate this method of regenerating spent aqueous caustic solutions containing alkali mercaptide compounds. They are presented for purposes of illustration only and are not intended to limit the scope of the invention.

EXAMPLE 6

The effectiveness of the catalyst of the invention in regenerating caustic solutions containing n-butanethiol and benzenethiol was first tested in the laboratory. In each of two runs, Run Nos. 1 and 3, 350 ml. of 10° Baume caustic was added to a 500 ml. three-necked flask fitted with a stirrer and gas dispersion tube extending into the caustic solution. The caustic was agitaed and purged with nitrogen gas at a rate of 450 cc/minute for approximately 5 minutes to remove dissolved air. In Run No. 1 n-butanethiol was then added to the caustic and in Run No. 3 benzenethiol was added. Sodium salt of Co-BTDA catalyst, prepared as illustrated in Example 1, was then added to each caustic sample and the mixture was purged with nitrogen gas for an additional 5 to 10 minutes with continued agitation. A sample of the liquid mixture was then withdrawn from each of the mixtures and analyzed to determine the original concentration of mercaptides present. In Run No. 1 the concentration of mercaptide was the equivalent of 2778 ppm of sulfur and the concentration of cobalt 5.6 ppm. In Run No. 3 the concentration of mercaptide was the equivalent of 4210 ppm of sulfur and the concentration of cobalt was 5.6 ppm. The flow of nitrogen through each of the liquid mixtures was discontinued and air flow at the rate of 450 cc per minute through each was begun. Samples of the mixture were removed at measured time intervals and analyzed for mercaptide concentration in ppm of sulfur by potentiometric titration. Corresponding tests, Runs 2 and 4, were also run with a commercial caustic regeneration-mercaptide oxidation catalyst marketed under the trade name Merox, by Universal Oil Products Co., Des Plaines, Illinois. In each of these latter runs the concentration of cobalt in caustic solution was 5.2 ppm. The data obtained from each of the four runs is reported in Table I.

The data shows that the oxidation rate of the mercaptide derived from benzenethiol is slightly lower than the oxidation rate of the mercaptides derived from n-butanethiol. The mercaptide benzenethiol is particularly difficult to oxidize, but when one considers the low concentration of this particular mercaptan occurring in gasoline streams to be treated, the Co-BTDA catalyst is sufficient to maintain a low level of mercaptide in the circulating caustic stream.

TABLE I

| | 1-butanethiol | | | | benzenethiol | | | |
|---|---|---|---|---|---|---|---|---|
| | Co-BTDA Catalyst Run 1 | | Merox Catalyst Run 2 | | Co-BTDA Catalyst Run 3 | | Merox Catalyst Run 4 | |
| Time Lapse Minutes | mls of sample | ppm of RSH* 2778 | mls of sample | ppm of RSH* 1900 | mls of sample | ppm of RSH* 4210 | mls of sample | ppm of RSH* 4167 |
| 0 | 0.5 | | 0.5 | | 0.5 | | 0.5 | |
| 2 | | | 0.5 | 1389 | 0.5 | | 0.5 | |
| 2.3 | 0.5 | 1389 | | | | | | |
| 2.5 | | | | | 0.5 | 3509 | 0.5 | 3728 |
| 5 | | | 1.0 | 219 | | | | |
| 5.5 | 1.0 | 585 | | | | | | |
| 7.5 | | | | | 0.5 | 3406 | 0.5 | 3655 |
| 8 | | | 3.0 | 49 | | | | |
| 10.0 | 3.0 | 0 | 5.0 | 0 | | | | |
| 12.5 | | | | | 0.5 | 3334 | 0.5 | 3363 |
| 17.5 | | | | | 0.5 | 3143 | 0.5 | 2814 |
| 22.5 | | | | | 0.5 | 2866 | 0.5 | 2376 |
| 27.5 | | | | | 0.5 | 2632 | 1.0 | 1864 |
| 32.5 | | | | | 0.5 | 2339 | 0.5 | 1645 |
| 37.5 | | | | | 0.5 | | | 1352 |
| 42.5 | | | | | 0.5 | 1864 | 1.0 | 1060 |
| 47.5 | | | | | 0.5 | 1608 | 2.0 | 819 |
| 52.5 | | | | | 0.5 | 1352 | | 618 |
| 57.5 | | | | | 0.5 | 1097 | 2.0 | 442 |
| 62.5 | | | | | 1.0 | 658 | 3.0 | 238 |
| 67.5 | | | | | 1.0 | 322 | | 85 |
| 70.0 | | | | | 2.0 | 192 | 3.0 | 0 |
| 75.0 | | | | | 3.0 | 73 | — | — |

*Concentration of RSH (mercaptide compounds) expressed as equivalent ppm of sulfur. The concentration of dissolved metal cobalt was 5.6 ppm in Runs 1 and 3, 5.2 ppm in Runs 2 and 4.

EXAMPLE 7

The effectiveness of the alkali metal salt of the vanadium complex prepared as described in Example 2 was treated in the laboratory. The following run is representative.

Five hundred ml. of 8.0° Baume caustic was added to a 1 liter flask equipped with a stirrer and gas dispersion tube. Gaseous nitrogen was bubbled through the caustic for about 10 minutes to purge dissolved air. Five ml. of 1-butanethiol and 0.5 grams of the sodium salt of the vanadium-BTDA complex were then added and the mixture was again purged with nitrogen. A 0.5 ml-sample of the mixture was then withdrawn and analyzed to determine the initial catalyst and mercaptan content.

Air at the rate of 450 cc per minute was then bubbled through the mixture. Samples were taken at intervals and analyzed for mercaptide concentration in terms of equivalent sulfur. Test results are shown in Table II. Although the oxidation rate of the vanadium complex was lower than that for the cobalt complex, its activity is still sufficient to function as an oxidation catalyst.

TABLE II

| SAMPLE NUMBER | TIME LAPSE, MINUTES | SAMPLE VOL, MLS. | RSH* PPM |
|---|---|---|---|
| 0 | 0. | .5 | 2304 |
| 1 | 8.0 | 1.0 | 2080 |
| 2 | 12.0 | .5 | 2240 |
| 3 | 16.2 | .5 | 2048 |
| 4 | 20.0 | .5 | 1952 |
| 5 | 24.0 | .5 | 1856 |
| 6 | 28.0 | .5 | 1760 |
| 7 | 32.0 | .5 | 1600 |
| 8 | 36.0 | .5 | 1600 |
| 9 | 40.0 | .5 | 1440 |
| 10 | 44.0 | .5 | 1216 |
| 11 | 48.0 | .5 | 1088 |
| 12 | 52.0 | .5 | 1088 |
| 13 | 56.0 | .5 | 960 |
| 14 | 60.0 | .5 | 832 |
| 15 | 64.0 | .5 | 704 |

*Determined as equivalent sulfur.

EXAMPLE 8

A column approximately 13 inches long and 1.9 inches in diameter representing a volume of 600 cc was filled with the catalyst prepared according to Example 5. Through this bed was flowed a mixed stream of 22° Baume caustic containing in solution 4.5 ppm of the cobalt-BTDA sodium salt complex, kerosene containing 130 ppm of sulfur in the form of mercaptans and air. The effluent liquids were collected in a separator where the caustic was recycled and the kerosene removed from the system. The concentration of mercaptans in the kerosene was reduced from 130 ppm of equivalent sulfur to 10 ppm. Other data is as follows:

| | |
|---|---|
| Column temperature | 77° F. |
| Column pressure | atmospheric |
| Flow rate of caustic, cc/minute | 8.3 |
| Flow rate of kerosene | 17.5 |
| LHSV of caustic | 0.865 |
| LHSV of kerosene | 1.82 |
| Ratio of caustic flow/caustic flow/cc per cc | 2.11/1.00 |
| Air flow, cc/minute | 400 |
| Mercaptan concentration in: | |
| Kerosene feedstock, ppm as sulfur | 130 |
| Kerosene effluent, ppm as sulfur | 10 |

EXAMPLE 9

The catalyst prepared according to Example 3 in the acid form was tested for its effectiveness in oxidizing mercaptans to didulfides as follows. Six milliliters of normal butylthiol were added to 500 milliliters of 8.0° Baume caustic solution in a flask fitted with a mechanical stirrer and tubing to admit and discharge air. Samples of the caustic solution were removed to determine the initial mercaptan concentration (3456-3434 ppm by weight of equivalent sulfur). One-tenth grams of the acid form of the catalyst were then added and air was bubbled through the liquid mixture at a rate of 400 to 450 cc per minute while the mixture was agitated. Periodically, samples of the mixture were withdrawn and analyzed for mercaptide concentration. Data obtained are shown in Table III which follows:

TABLE III

| SAMPLE NO. | TIME MINUTES | MERCAPTIDE CONCENTRATION* |
|---|---|---|
| 1 | 0 | 3456** |
| 2 | 0 | 3424 |
| 3 | 0 | 2496*** |
| 4 | 2.75 | 2240 |
| 5 | 7.50 | 1856 |
| 6 | 15.00 | 1120 |
| 7 | 20.0 | 440 |
| 8 | 25.0 | 272 |
| 9 | 30.0 | 89.6 |
| 10 | 35.0 | 25.6 |

*ppm of equivalent sulfur
**before addition of catalyst
***catalyst added and air injection

We claim:

1. A method for oxidizing mercaptans occurring in petroleum hydrocarbon distillates and alkali mercaptide compounds occurring in aqueous alkaline solutions, said compounds resulting from contacting aqueous alkaline solutions with said distillates containing mercaptans, to their corresponding disulfide compounds comprising contacting said mercaptans and mercaptide compounds in an aqueous alkaline solution with a gaseous oxidizing agent and with a catalyst comprising a metal complex of 2,3,7,8,12,13,17,18-tetra [1,2-benzo-4 (4'-phthaloyl)]—porphyrazine-2,22,23,24-tetraene, or a substituted derivative thereof having the structural formula:

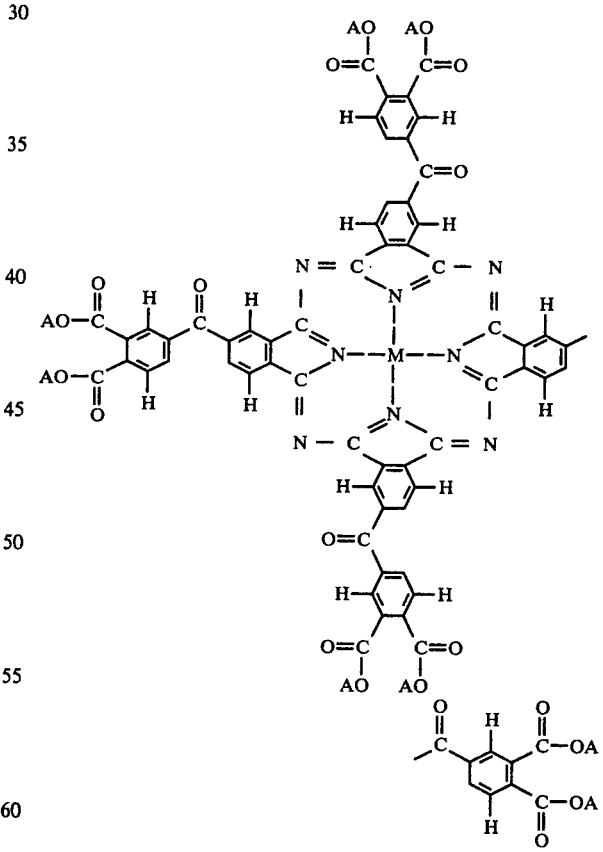

where M is a metal selected from the group consisting of iron, manganese, chromium, magnesium, copper, nickel, zinc, titanium, hafnium, thorium, tin, lead, columbium, tantalum, antimony, bismuth, molybdenum, palladium, platinum, silver, mercury, vanadium and cobalt and A is hydrogen or an alkali metal.

2. The method of claim 1 wherein said metal M is cobalt and A is hydrogen.

3. The method of claim 1 wherein said metal M is cobalt and A is selected from the group consisting of sodium, potassium, and mixtures thereof.

4. The method of claim 1 wherein said metal M is cobalt.

5. The method of claim 1 wherein said metal M is vanadium.

6. The method of claim 1 wherein said contacting is conducted at a pressure of between about 10 and about 100 psig, a temperature of between about 50° and about 150° F., and a ratio of between about 0.25 and about 1 mole of oxygen in said oxidizing gas per mole of mercaptan and alkali mercaptide compounds.

7. The method of claim 1 and the additional step of separating oxidized mercaptide compounds (disulfide) from said aqueous alkaline solution.

8. The method of claim 1 wherein said gaseous oxidizing agent is air.

9. The method of claim 1 wherein said gaseous oxidizing agent is a mixture of oxygen and a nonreactive gas.

10. The method of claim 1 wherein said metal complex is supported on a solid granular inert carrier.

11. The method of claim 1 wherein:
 a. said aqueous alkaline solution is an aqueous sodium hydroxide solution;
 b. said gaseous oxidizing agent is air supplied in a ratio of at least 0.25 moles of oxygen in said air per mole of mercaptides and mercaptans;
 c. the pressure is between about 10 and about 100 psig;
 d. the temperature is between about 50° and about 150° F.;
 e. the liquid-space velocity is about 0.1 and about 20 volumes of aqueous sodium hydroxide solution per volume of catalyst per hour; and
 f. said catalyst comprises said metal complex impregnated on granular activated carbon in an amount of at least 0.5 percent by weight of the catalyst, M is a metal selected from the group consisting of cobalt and vanadium, and A is an alkali metal.

12. The method of claim 10 wherein said metal M is cobalt.

13. The method of claim 10 wherein said metal M is vanadium.

14. The method of claim 10 wherein said contacting is conducted at a pressure of between about 10 and 100 psig. a temperature of between about 50° and about 150° F., a liquid-hourly-space velocity of between 0.1 and about 20 volumes of aqueous alkaline solution per volume of catalyst per hour and a ratio of between about 0.25 and about 1 mole of oxygen in aid oxidizing gas per mole of mercaptan and alkali mercaptide compounds.

15. The method of claim 10 and the additional step of separating oxidized mercaptide compounds from said aqueous alkaline solution.

16. The method of claim 10 wherein said gaseous oxidizing agent is air.

17. A method for oxidizing mercaptans occurring in petroleum hydrocarbon distillates and alkali mercaptide compounds occurring in an aqueous sodium hydroxide solution, said compounds resulting from contacting said aqueous sodium hydroxide solution with said distillates containing mercaptans, to their corresponding disulfide compounds, comprising contacting said aqueous solution of sodium hydroxide with air in a ratio of at least 0.25 moles of oxygen in said air per mole of mercaptide and mercaptans, at a pressure of between about 10 psig and about 100 psig, a temperature of between about 50 and about 150° F. and with a catalyst comprising a metal complex of 2,3,7,8,12,13,17,18-tetra [1,2-benzo-4 (4'-phthaloyl)]-porphyrazine-2-,22,23,24-tetraene or a substituted derivative thereof having the structural formula:

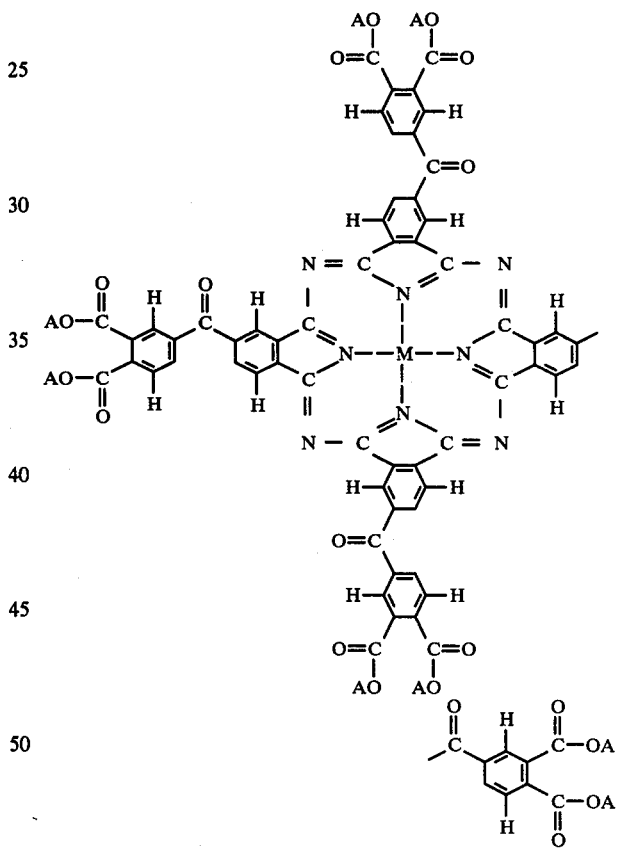

where M is a metal selected from the group consisting of cobalt and vanadium and A is selected from the group consisting of hydrogen, sodium and potassium.

* * * * *